US00PP27061P2

(12) United States Plant Patent
Pluta et al.

(10) Patent No.: US PP27,061 P2
(45) Date of Patent: Aug. 16, 2016

(54) BLACK CURRANT PLANT NAMED 'POLARES'

(50) Latin Name: *Ribes nigrum*
Varietal Denomination: Polares

(71) Applicants: Stanislaw Pluta, Skierniewice (PL); Edward Zurawicz, Skierniewice (PL)

(72) Inventors: Stanislaw Pluta, Skierniewice (PL); Edward Zurawicz, Skierniewice (PL)

(73) Assignee: Instytut Ogrodnictwa, Skierniewice (PL)

( * ) Notice: Subject to any disclaimer, the term of this patent is extended or adjusted under 35 U.S.C. 154(b) by 178 days.

(21) Appl. No.: 13/998,932

(22) Filed: Dec. 23, 2013

Related U.S. Application Data

(60) Provisional application No. 61/848,162, filed on Dec. 26, 2012.

(51) Int. Cl.
*A01H 5/08* (2006.01)

(52) U.S. Cl.
USPC ..... Plt./156

(58) Field of Classification Search
USPC ..... Plt./156
See application file for complete search history.

(56) References Cited

PUBLICATIONS

Labanowska et al. Journal of Fruit and Ornamental Plant Research 18(2): 283-295, 2010.*

* cited by examiner

*Primary Examiner* — Keith Robinson
(74) *Attorney, Agent, or Firm* — Penny J. Aguirre

(57) ABSTRACT

A new cultivar of *Ribes nigrum*, 'Polares', that is characterized by its upright, medium tall plant habit and weak to moderate plant growth and vigor, its moderate fruit productivity, its small to medium sized fruit, its high quality fruit that is high in acidity, anthocyanin concentration, and ascorbic acid content, its high resistance n the field to powdery mildew (*Sphareotheca mors-uvae*) and full resistance gall mite (*Cecidophyopsis ribis*), and its very good winter hardiness.

2 Drawing Sheets

Botanical classification: *Ribes nigrum.*
Cultivar designation: 'Polares'.

BACKGROUND OF THE INVENTION

The present invention relates to a new and distinct cultivar of *Ribes nigrum* named 'Polares' and is hereinafter referred to by the cultivar name 'Polares'. 'Polares' represents a new cultivar of black currant grown for fruit production.

The new cultivar was derived from a controlled breeding program by the Inventors in Skierniewice, Poland. The Inventors made a cross in 1994 between unnamed proprietary plants in the Inventor's breeding program, reference no. S 12/3/83 as the female parent and reference no. EMB 1834/113 as the male parent. The Inventor selected 'Polares', breeding reference no. PC-7/13, in 2000 as a single unique plant amongst the seedlings that resulted from the above cross.

Asexual propagation of the new cultivar was first accomplished by one of the Inventors by hardwood cuttings in Skierniewice, Poland in 2012. Asexual propagation by hardwood cuttings has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Polares' as a new and unique cultivar of *Ribes nigrum.*

1. 'Polares' exhibits an upright, medium tall plant habit and moderate plant growth and vigor.
2. 'Polares' exhibits moderate fruit productivity.
3. 'Polares' exhibits small to medium sized fruit.
4. 'Polares' exhibits high quality fruit that is high in acidity, anthocyanin concentration, and ascorbic acid content
5. 'Polares' exhibits high resistance in the field to powdery mildew (*Sphareotheca mors-uvae*) and full resistance to gall mite (*Cecidophyopsis ribis*).
6. 'Polares' exhibits very good winter hardiness.

'Polares' can be readily compared to its parent plants. S 12/3/83, the female parent, differs from 'Polares' in having more vigorous plant growth, in having a less upright plant habit, in having decreased fruit quality and productivity, and in being susceptible to powdery mildew (*Sphareotheca mors-uvae*) and gall mite (*Cecidophyopsis ribis*). EMB 1834/113, the male parent, differs from 'Polares' in having a less upright plant habit, in having decreased fruit quality and productivity, and in being much less resistant to fungal diseases. 'Polares' can be most closely compared to the *Ribes* cultivars 'Ben Alder' (U.S. Plant Pat. No. 9,889) and 'Ben Lomond' (not patented). 'Ben Alder' is similar to 'Polares' in having moderate plant growth and vigor, in having high quality, small to medium sized fruit, and in its fruit ripening time. 'Ben Alder' differs from 'Polares' in having a less upright plant habit, in being more susceptible to fungal diseases and gall mite, and in being less winter hardy. 'Ben Lomond' is similar to 'Polares' in having weak plant vigor, in having moderate fruit productivity, and in its fruit ripening time. 'Ben Lomond' differs from 'Polares' in having a less upright plant habit, in having lower quality fruit, in being more susceptible to fungal diseases and gall mite, and in being less winter hardy.

BRIEF DESCRIPTION OF THE DRAWINGS

The accompanying colored photographs illustrate the overall appearance and distinct characteristics of the new *Ribes* cultivar. The photographs were taken of three year-old plants of the new cultivar as grown outdoors in a field in Skierniewice, Poland.

The photograph in FIG. 1 provides a view of the plant habit of 'Polares'.

Figure 1:
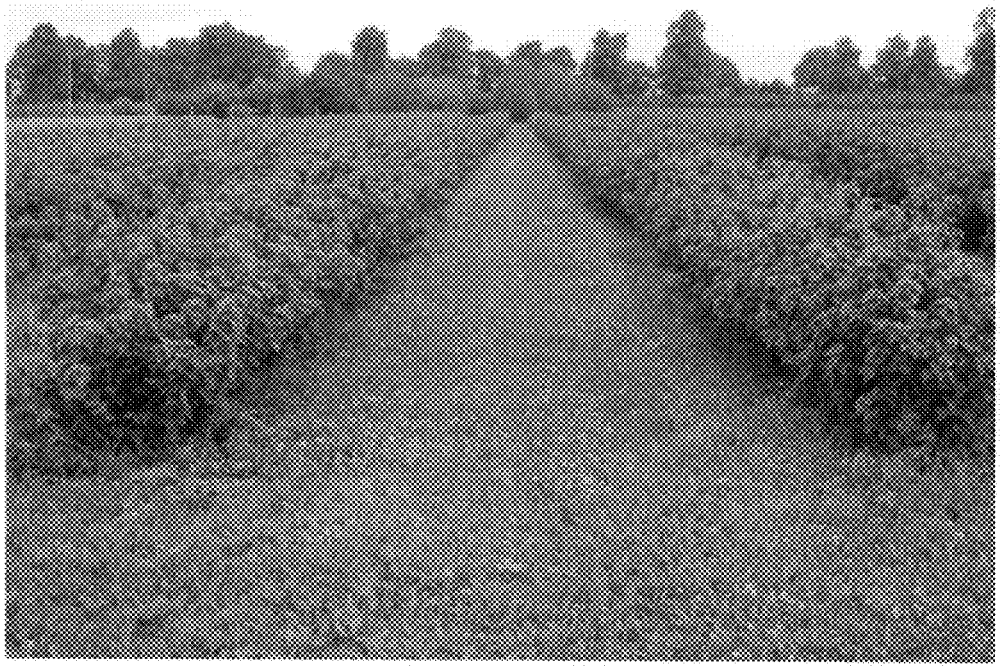
Figure 2:
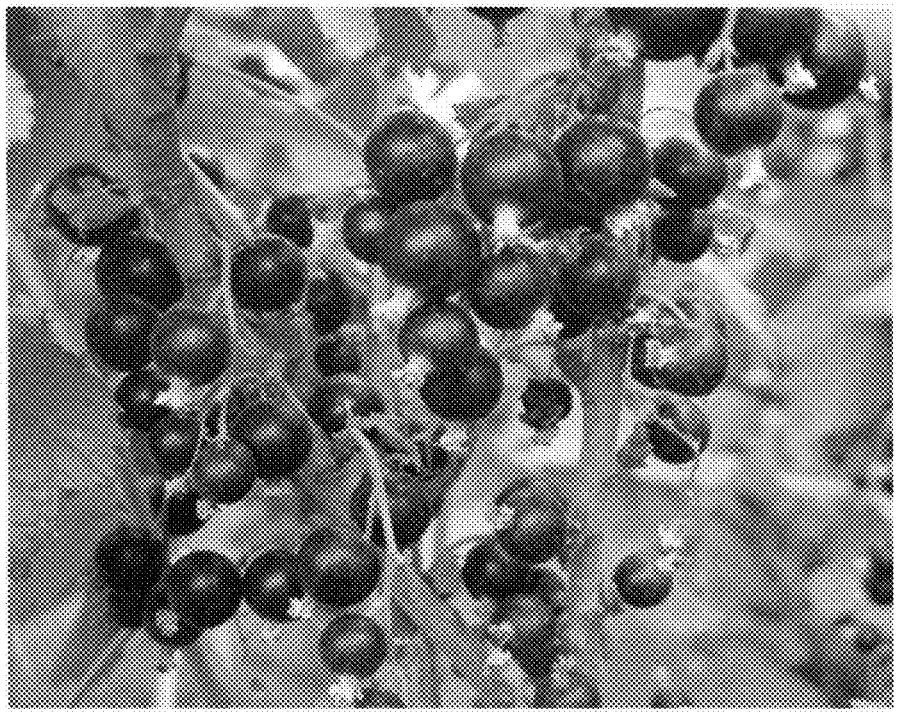

The photograph in FIG. 2 provides a close-up view of a fruiting branch of 'Polares'.

Figure 3:
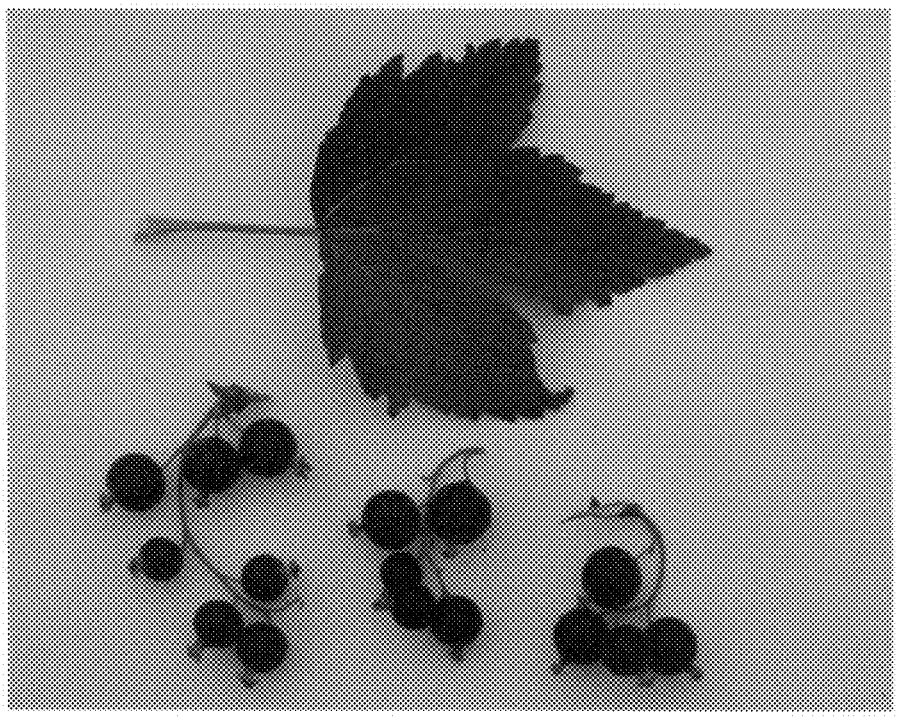

The photograph in FIG. 3 provides a close-up view of mature fruit and a mature leaf of 'Polares'.

The colors in the photographs are as close as possible with digital photography techniques available, the color values cited in the detailed botanical description accurately describe the colors of the new cultivar of *Ribes*.

DETAILED BOTANICAL DESCRIPTION OF THE PLANT

The following is a detailed description of plants three years in age as grown outdoors in a trial field in Skierniewice, Poland. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Late April to early May in central Poland.

*Plant type.*—Perennial, fruit producing shrub.

*Plant habit.*—Upright and medium tall.

*Height and spread.*—Reaches about an average of 0.95 m in height and 1.35 m in width.

*Cold hardiness.*—At least in U.S.D.A. Zone 6.

*Diseases and pests.*—High resistance in the field to powdery mildew (*Sphareotheca mors-uvae*) and full resistance to gall mite (*Cecidophyopsis ribis*) has been observed.

*Roots.*—Fibrous and 162D in color.

*Root development.*—About 10 days to initiate roots and 2 months to produce a young rooted plant.

*Propagation.*—Hardwood cuttings.

*Growth rate.*—Moderate.

Stem description:

*Stem.*—Strong, mature stem 177B and 196B and 198C in color; new growth, 144A in color, surface is smooth on new growth and smooth bark-like when mature, main branches up to 78 cm in length and an average of 25 cm in width.

*Stem number.*—An average of 20 basal shoots per 3 year-old plant.

*Leaf bud shape.*—Obclavate, bracts imbricate.

*Leaf bud size.*—Average of 0.70 cm in length, 0.33 in width.

*Leaf bud position relative to shoot.*—Slightly held out.

*Leaf bud burst.*—Begins in late March to early April in Poland.

*Leaf bud apex.*—Rounded.

*Number of leaf buds.*—On a 50 cm long stem; an average of 19.4 buds, ranging from 18 to 20 buds per stem.

*Bracts.*—Deltoid in shape, apex retuse to subacute, base truncate, average 15 mm in width, 30 mm in length, margin entire and fimbriate, young inner surface 145A, flushed with 181A in color, young outer surface 145A in color, older bracts inner and outer suface 181A in color.

Foliage description:

*Leaf shape.*—Five-lobed, with extended central lobe.

*Leaf division.*—Simple, not divided.

*Leaf base.*—Weakly opened.

*Leaf apex.*—Subacute.

*Leaf venation.*—Pinnate, color on upper and lower surface 142A.

*Leaf margins.*—Subacute to acute lobed with lobe margins serrate.

*Leaf attachment.*—Petiolate.

*Leaf arrangement.*—Alternate clusters.

*Leaf orientation.*—Slightly downwards.

*Leaf surface.*—Upper surface glabrous and dull, lower surface slightly puberulent with fine minute hairs and glandular, neither surface is glossy.

*Leaf color.*—Young upper surface; a blend of N144A and 143A, young lower surface; N144A, mature upper and lower surface; 143A to 143B.

*Leaf size.*—Medium to large, an average of 11.0 cm in length, an average of 11.5 cm in width.

*Leaf quantity.*—About 25 per 79 cm of stem length.

*Petioles.*—Flat to round in shape, an average of 4.2 cm in length and 2.5 mm in width, a blend of 143A and 149A, surface smooth.

*Stipules.*—None observed.

Inflorescence description:

*Bloom season.*—Approximately 28 April to 8 May in Skierniewice, Central Poland.

*Inflorescence.*—Drooping raceme of single flowers, average of 3.5 cm in length and 1.0 cm in width, 14 (no.) racemes per stem 30.0 cm in length.

*Lastingness of inflorescence.*—8 to 12 days depending on weather conditions at time of bloom.

*Pedicels.*—Round in shape, strong, 1-2 mm in width, 30 mm in length, color; a blend of 149B and 181A, surface texture smooth.

*Peduncles.*—Round in shape, strong, an average of 0.5 cm in length and 0.5-0.8 mm in width, surface texture smooth, color; a blend of 143A and 181A and 180A, turning 150A towards the tip.

*Flowers.*—Campanulate, 8 to 11 (no.) flowers per raceme.

*Flower buds.*—Ovate in shape, 4.2 to 6.0 mm in length, 3.8 mm in width, color; middle section a blend of 149A and 145C, base is 145A, suffused with 178A.

*Flower size.*—Average of 5.8 mm in length, 5.8 mm in width.

*Flower number.*—An average of 10 flowers per raceme (inflorescence).

*Sepals.*—5, strongly recurved, 1 mm in width, 2 mm in length fused at base, color on outer and inner surface; a middle section N144C, tips a blend of 63C, 75B and 73A, suffused with 178A at the base in color, rounded apex, margins entire, sparsely pubescent on upper surface and pubescent on lower surface.

*Petals.*—5 (quantity) fused in hypanthium, 3-4 mm in length, 2-3 mm in width, 145B to 145C in color on inner and outer surface, upper surface smooth (texture) and smooth (texture) lower surface.

*Androecium.*—Epipetalous, anthers are ovate (shape), 11C in color, 0.5 mm in length, 0.8 mm in width, filaments are 2-3 mm in length, 0.5-0.6 mm in width, 11D in color.

*Gynoecium.*—Five fused in hypanthium, style is 3-4 mm in length, 0.5-0.6 mm in width, 14BA in color in color, ovary is inferior, 2-3 mm in length and 2-3 mm in width, round in shape, 145B in color bifid stigma is minute and 145B in color.

Fruit description:

*Fruit number.*—64 to 78 fruits per branch 62 cm long.

*Fruit yield.*—1.40 kg per plant in Skiemiewice, Poland (location) on 5 year-old plants.

*Fruit set.*—High, 75%.

*Fruit size.*—Small to medium, average of 0.47 cm in diameter and 0.46 cm in height.

*Fruit weight.*—Ranges from 0.6 to 0.8 g/berry.

*Fruit chemistry.*—High in acidity, anthocyanins, and ascorbic acid, averages: Brix 17.4, specific gravity, 21.4 g/L citric, anthoncyanins 436 (517 nm), ascorbic acid 290 mg/100 g.

*Position of maximum diameter.*—Midway between proximal and distal ends.

*Fruit shape.*—Globose.

*Fruit symmetry.*—Symmetric.

*Persistence of calyx.*—Persistent at harvest, brown in color, 1.5 mm in length.

*Surface.*—Glossy, smooth except for slightly protruding lenticels.

*Lenticels.*—18 to 55 per fruit, 198D in color.

*Waxiness of skin.*—Very light.

*Thickness of skin.*—Moderately thick.

*Skin color.*—Immature 145A, maturing 181A, mature 202A.

*Color of flesh.*—N79A.

*Fruit maturity date.*—Mid to late fruit ripening, first harvest date about 20 July, range of harvest period 10 days.

*Seed.*—Oblong in shape, 35 per fruit, 2.0 mm in length, 1.1 mm in width, 200C in color.

*Firmness* (*without skin*).—Firm.

*Texture of flesh.*—Pulpy, juicy.

*Cropping frequency.*—Regular.

*Flavor.*—Good (slightly acid).

*Fruit use.*—Particularly suitable for use in processing (concentrates and juices).

*Juice yield.*—17.8 ml/100 berries.

*Fruit keeping quality.*—Very good.

It is claimed:

1. A new and distinct cultivar of *Ribes nigrum* plant named 'Polares' as herein illustrated and described.

* * * * *